United States Patent [19]

Ganglbauer et al.

[11] Patent Number: 4,744,250
[45] Date of Patent: May 17, 1988

[54] METHOD FOR CLASSIFICATION OF POINT AND ELONGATED SINGLE DEFECTS IN WORKPIECES BY MEANS OF ULTRASONICS

[75] Inventors: Otto Ganglbauer; Josef Ausserwöger; Felix Wallner, all of Linz, Austria

[73] Assignee: Voest-Alpine Aktiengesellschaft, Muldenstrasse, Austria

[21] Appl. No.: 909,888

[22] Filed: Sep. 22, 1986

[30] Foreign Application Priority Data

Oct. 3, 1985 [AT] Austria ................................. 2866/85

[51] Int. Cl.$^4$ ............................................ G01N 29/04
[52] U.S. Cl. ......................................... 73/588; 73/602
[58] Field of Search .................... 73/588, 602; 364/508

[56] References Cited

U.S. PATENT DOCUMENTS 4,531,409  7/1985  Koch et al. ............................ 73/588

Primary Examiner—Jerry W. Myracle
Attorney, Agent, or Firm—Cushman, Darby & Cushman

[57] ABSTRACT

In a method of flaw classification on and in welds of planar or arcuate plate-shaped workpieces of uniform thickness by means of ultrasonics, the expected flaw areas of the workpiece are pre-examined manually and are then examined systematically using the ultrasound echo image method in separate cross-sectional planes. A B-scan is thus generated, and changing the position of the transducer on the workpiece and/or the transmitting direction enables defects to be located by calculating the delay time of ultrasound waves in the go-and-return directions within the workpiece under consideration of possible reflections at the rear side (8) of the workpiece. For defining the test conditions, part-specific parameters are considered, such as weld type and weld shape (e.g., double-V-weld and bell seam), weld geometry (e.g. seam angle), and part characteristics (e.g. wall thickness), whereupon with the aid of a computer into which the parameters have been inputted, a graphic representation corresponding to a B-scan is generated. In the graphic representation at least one area, in which the density of obtained reflection points per unit of area exceeds a predetermined value, is surrounded by a closed curve of second order, generally an ellipse, and the angular direction of a privileged axis, particularly the major axis of the ellipse, in relation to a reference system, the axis ratio and/or the center location are calculated. Reflection points, located opposite from each other, of a defect are detected, and the ratio between length and thickness of the defect or the orientation tendency, respectively, is calculated, whereupon at least by logically linking orientation tendency and path difference a discrimination between volumetric-type defects, planar defects and a combination of such defects is brought about.

4 Claims, 3 Drawing Sheets

METHOD FOR CLASSIFICATION OF POINT AND ELONGATED SINGLE DEFECTS IN WORKPIECES BY MEANS OF ULTRASONICS

BACKGROUND OF THE INVENTION

1. Field of the Invention

The invention relates to a method of flaw classification in workpieces, particularly on and in welds of planar or arcuate parts having a known course of thickness, by means of ultrasonics in which a systematical test of the workpiece or its expected flaw areas, respectively, pre-examined manually or mechanizedly if desired, is carried out by using the ultrasound echo image method in separate cross-sectional planes for generating a cross-sectional or B-scan, changing the position of the transducer means on the workpiece and/or the transmitting direction, and calculating the delay times of possible reflections for locating defects.

2. Description of the Prior Art

For non-destructive testing of materials, semi-finished products and finished parts, ultrasonic methods have been in use for quite some time. In connection with the ultrasound echo image method and representation of the result on the screen of a cathode ray tube, there are the possibilities either of generating an A-scan (linear method), where simultaneously with the sound pulse the X-deflection of the cathode ray tube is started and the strength of the received echo effects a Y-deflection so that the abscissa of the blip on the screen contains information above the delay time and thereby the distance between the reflector location and the transmitter location, or of generating a B-scan for a surface representation of a section through the tested body in which reflectors are shown by trace-unblanking. Interpretation of the image in the latter case depends on the experience of the observer.

It has to be an object of any product inspection the production process or of testing parts being in use to provide all information which is either criteria for evaluation of the condition of a product at delivery with respect to a prescribed acceptance standard or is useful for evaluation of the suitability of a part of a machine or of a plant for its further use. While essential advantages of ultrasound technology are the reliable detection and location of internal flaws in materials, and wherein estimation of flaw dimensions can be carried out satisfactorily with certain methodological restrictions, imperfections of ultrasonic testing in the past were due to the qualitative, i.e. flaw-type related interpretation of the natural flaw. Because of an ever growing safety demand and increasing testing activity concerning product tests during production as well as particular tests of highly loaded parts and plants such as high pressure pipe lines, bridge girders and the like, an answer about the flaw type is of essential importance.

It it is rendered possible to classify the flaw type with certainty, on the one hand the affect of a flaw on a construction can be estimated more exactly, but on the other hand, in many cases, particularly in connection with periodical routine inspections of plants in operation, some information can be derived when or under which circumstances a defect might have occured.

With a method for non-destructive testing of a workpiece by means of ultrasonics known from DE-PS No. 32 36 017, it has been tried to render visible with high resolution the shaft of a defect enclosed in the material. This is carried out by utilization of a clocked array of built-up ultrasound transducers, whereby the transmitting direction or angle, respectively, of the array can be varied cyclically, the ultrasound signals being transmitted into a workpiece whose delay time to the reflector on the contour of the defect and the corresponding amplitude are detected and stored. In a second memory, delay time and amplitude of possible locations in the expected flaw area are stored in such a way that only maximum values are written into the memory. The result is then shown on a visual display unit in the form of an intensity distribution (conglomeration of reflection points), wherein one can see where there are essential defects and where there are defects which might be neglected. When applying this known method, information can be obtained as to where in the workpiece there is some discontinuity and which geometric shape the defect indicated by the discontinuity has, based on the measured reflection points. With regard to the type of defect, however no information can be obtained because any connection with the production technology of the workpiece is missing.

Another way of classifying defects occurring in welded plates is disclosed by the article "Flaw Classification in Welded Plates Employing a Multidimensional Feature-based Decision Process" in the periodical *Materials Evaluation*, Vol. 42, No. 4, pp. 433–438, 443. In accordance with the method disclosed therein, the amplitude of ultrasound echos is recorded while continuously changing the position of the ultrasound transducer or the transmitting direction (angle of impingement), or a magnitude derived from the echo amplitude is recorded in relation to one of the variables or to the delay time between ultrasound transducer and reflector location. Depending on the rate of rise or fall of the echo amplitude at the leading and trailing edges on both sides of a reflector, certain conclusions can be drawn concerning the types of defects, such as cracks, porosities or slags. For rendering possible an objective exploitation of the measuring data when testing a weld, the geometric shape of the weld has to be known since otherwise processing of the measuring data becomes intricate. Therefore, e.g. for testing a double-V weld, the cross-section of the weld is divided into four zones to which the different measuring data are to be allocated. Under such conditions 75% or more of the defects could be identified correctly. With the aid of the known method in expected flaw areas whose extent has to be known at the beginning, the presence of defects can be determined and the type of typical defects can be identified. However, there is not foreseen any type of graphic reproduction for displaying the extent of flaw areas.

SUMMARY OF THE INVENTION

It is an object of the present invention to provide a method of flaw classification in workpieces in which, after a search for expected flaw areas by a manual pre-examination, if desired, an evaluation of the determined defects is carried out by way of a graphic representation of the defect where extent and location of the defect in a selected cross-section can be seen.

For solving this problem the method of the present invention is characterized in that after inputting constructional and welding-technological parameters and part-specific test conditions, a graphic representation is drafted with the aid of a computer, where in the graphic representation at least one area containing a predetermined number of reflection points is surrounded by a closed curve, particularly a curve of second order. The closed curve may have the angular direction of a privileged axis, particularly the major axis of an ellipse, in relation to a reference system, the so-called orientation, the axis ratio or ratio between length and thickness of the defect, and the center location being calculated therefrom. Starting from the determined orientation, the path difference between two reflection points of a defect, located oppositely to each other, is detected, and by logically linking axis ratio, path difference, orientation, center location and projected defect height with welding-technological and constructional parameters as well as consideration of defect position, a discrimination between the different volumetric-type defects, the different planar defects and the different combinations of such defects is brought about.

By combined application of the afore-mentioned measures, one is enabled not only to differentiate between, e.g., cracks, cavities and slags, but by encircling a conglomeration of reflection points with a closed curve, generally an ellipse, the extent, location and orientation of a defect can be recognized in their essential outlines at a glance.

For scanning the defect with ultrasonics in a practicable economical way from different sides, in accordance with a further development of the method, based on the determined parameters of the closed curve, particularly the angular direction of the major axis of an ellipse, two additional positions of the transducer means are appointed for detecting a path difference for determining the thickness of the defect.

For conducting the dialog for the discrimination between the different volumetric-type defects, the different planar defects and the different combinations of such defects, preferably characteristic parameters of the curve of second order, such as length of the major axis, length of the minor axis, the ratio between both axes, inclination of the major axis in relation to the test surface, location of the center in a defined coordinate system, maximum dimensions of the figure of second order projected on one plane each normal and parallel, respectively, to the test surface are determined.

BRIEF DESCRIPTION OF THE DRAWING

The invention will become more readily apparent from the following detailed description in conjunction with the drawings, in which.

DESCRIPTION OF THE PREFERRED EMBODIMENT

Figure 1:
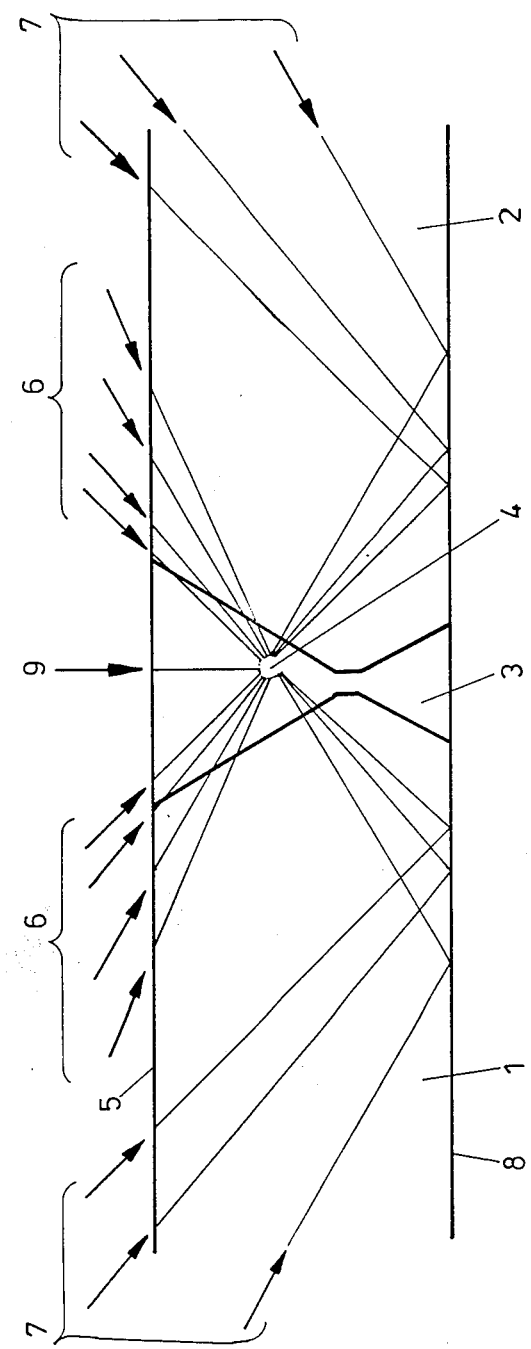
FIG. 1 is a cross-section of a weld connecting two flat plates showing different transmitting directions (angles of impingement) to be applied successively for the test by means of ultrasonics.

FIG. 1 shows a connection of two metal plates 1 and 2 by means of a double-V weld 3 in cross-section. There is a defect 4 within the weld 3. The defect 4 is scanned by beams of ultrasonic energy in the upper hemisphere from the front side 5 of the plates in different directions 6 directly, and in the lower hemisphere the defect 4 is also scanned from the front side 5 in different directions 7 after reflection on the rear side 8 (half jump). In addition, a beam direction 9 normal to the front side 5 can be chosen whereby minimum distance between the defect 4 and the front side 5 can be measured.

The separate "shots" are shown in a graphic representation of the weld cross-section on a visual display unit to inform the tester. Besides a representation of the defect in a cross-sectional plane, if need be, several such cross-sectional planes can be combined for displaying the defect. The evaluation of the separate "shots" is the basis for determining the main orientation of the defect in a subsequent calculating process. In the graphic representation, the totality of all reflectors is shown as a field of points which thereafter is surrounded with a closed curve of second order that usually will be an ellipse.

In the examination of parts and plants, their ability for the first use or for continued use has to be evaluated. A condition therefor is that as much information as possible be used when describing the defect regarding its type, orientation and shape. Besides the parameters of the defect, other specific criteria have to be taken into consideration for evaluating the useability. In addition to orientation within the cross-section, the location within the cross-section and the location of the defect at the part as well as the probability density must be evaluated. Material properties, the stress under use, operating conditions and prescribed safety factors belong to the decision criteria for the useability. Empirical values relating to the behaviour in operation are of interest, too.

Figure 2:
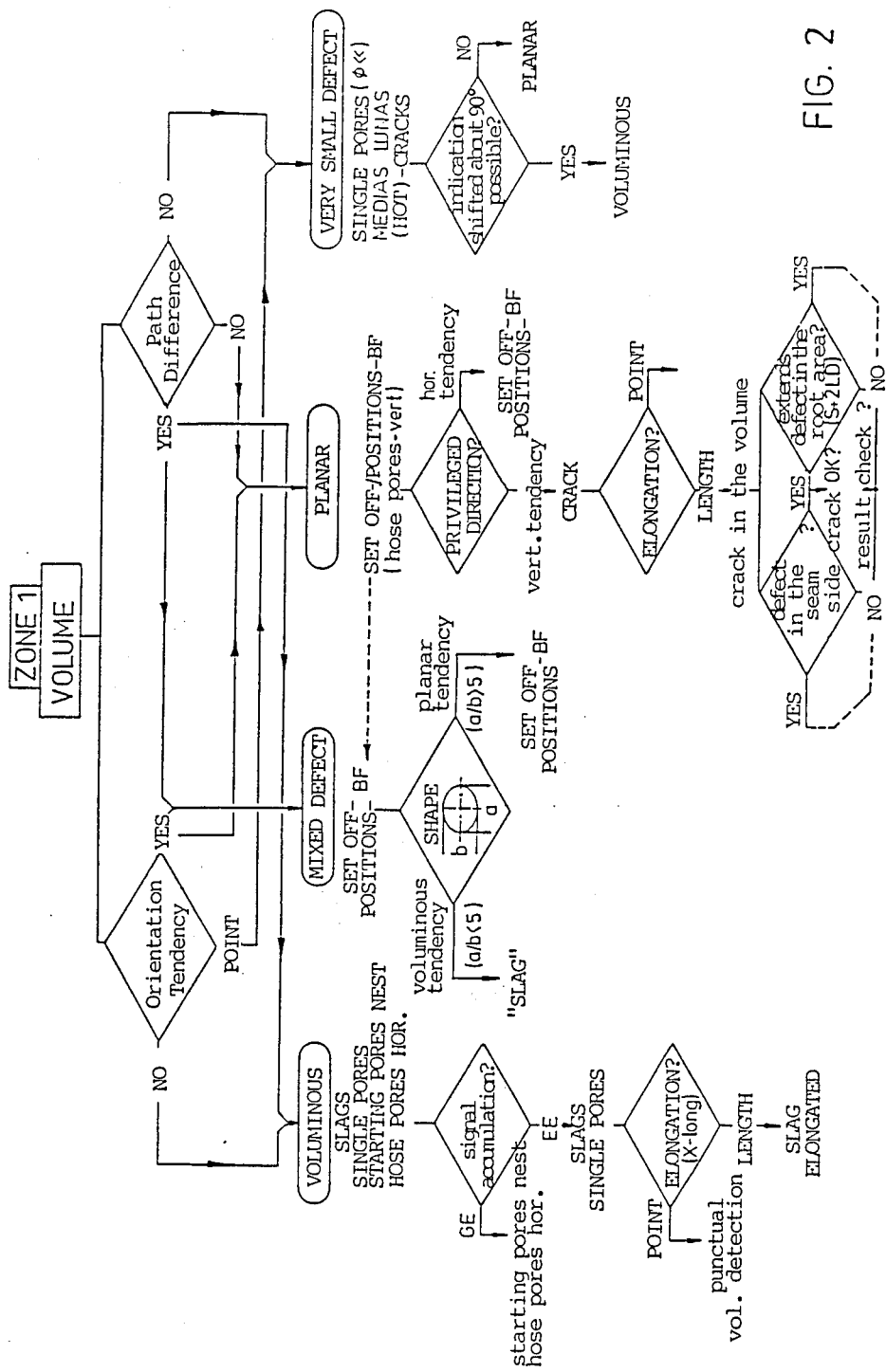
FIG. 2 shows a flow chart of the test course.

FIG. 2 shows a flow chart for a computer-aided method of operation. On demand the number of steps can be different. It is possible to carry on the diagnosis e.g., up to a differentiation between planar and volumetric-type defects. If, however, a further differentiation between specific defect types within one of the two classes is desired, further decision steps can be added. Thereby high flexibility of adaptation to a certain testing problem is achievable.

Figure 3:
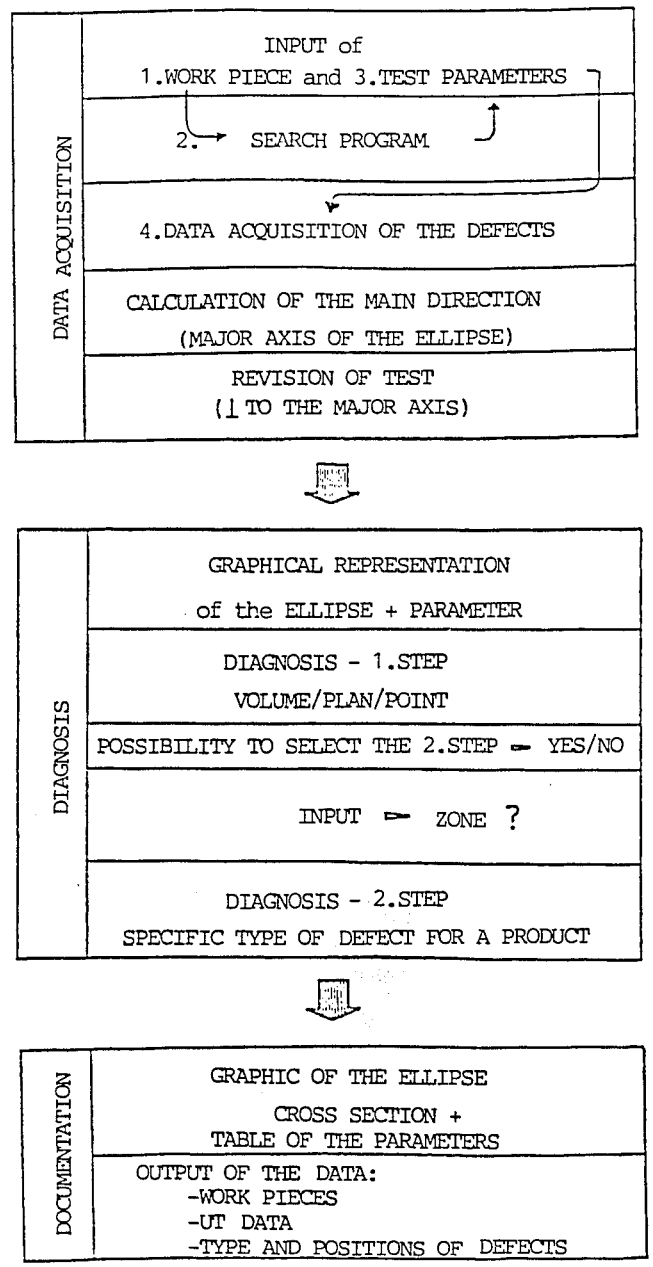
FIG. 3 shows the principal structure of the diagnosis software.

In practice, prior to each systematic examination in accordance with the flow chart of FIG. 2, a so-called manual examination will be preformed. This is a well-known standard test with manual testing equipment using two or more angle probes, usually having transducer angles between 35 and 70 degrees, for obtaining information whether and where on and in the workpiece there are any flaws, and whether they conform to any given test specification or cannot be defined clearly, so that a systematic examination has to be carried out subsequently. The computer-aided test is started by a search and information program by which those defects shall be located which had been found during manual examination, and information characterizing the defect shall be outputted. By such a sequence of the testing steps the abilities of man, such as skill in the art and experience, and equipment (computer) are combined to obtain an improved qualitative interpretation of ultrasonic test results. A preferred base structure of the diagnosis software therefor is shown in FIG. 3.

The method of the present invention is particularly suitable for borderline cases in evaluating quality or useability of parts and plants. Its function is directed to guide the tester in the form of a programmed dialog for finding decisions and to process and edit all information necessary for the tester objectively. The decisions about the necessary inputs in the dialog now as before are a matter to be handled by the tester oriented on the principles of manual examination so that skill in the art and experience of the tester come fully into effect.

We claim:

1. A method of classifying flaws in a workpiece, particularly on and in welds of planar or arcuate parts of said workpiece, said parts having a known thickness, comprising the steps of:

systematically testing said workpiece for flaws by generating first ultrasound echo images of said workpiece for separate cross-sectional planes of said workpiece, thereby obtaining a first cross-sectional representation of said workpiece;

changing at least one of a position of a transducer which generates said first ultrasound echo images of said workpiece and a transmitting direction of ultrasonic signals used in generating said first ultrasound echo images of said workpiece;

systematically testing said workpiece for flaws by generating second ultrasound echo images of said workpiece for said separate cross-sectional planes of said workpiece, thereby obtaining a second cross-sectional representation of said workpiece;

calculating delay times of reflection components of said first and second cross-sectional representations from reflection points of said workpiece so as to locate particular flaws in said workpiece;

generating a graphic representation of at least one area of said workpiece containing a predetermined number of said reflection points;

surrounding said graphic representation of said at least one area of said workpiece with a closed second order curve, said curve approximating the size and shape of said at least one area of said workpiece;

determining an orientation of a major axis of said curve with respect to a reference system of the workpiece, an axis ratio of the length and width of said curve, and a center location of said curve;

starting from said determined orientation, detecting a path difference between two reflection points located opposite from each other for one of said particular flaws; and processing said axis ratio, said path difference, said determined orientation, said center location and a projected height of said one particular flaw with predetermined parameters and the position of said at least one area of said workpiece in the reference system of the workpiece so as to determine at least whether said one particular flaw is one of a volumetrictype defect, a planar defect, and a combination of a volumetrictype and a planar defect.

2. The method as claimed in claim 1, wherein said closed second order curve is an ellipse.

3. The method as claimed in claim 2, wherein said determining step includes the step of determining characteristic parameters of said ellipse, said parameters comprising the length of said major axis, the length of a minor axis, the axis ratio of said major and minor axes, inclination of said major axis with respect to a test surface of said workpiece, location of said center of said ellipse in said reference system, and maximum dimensions of said ellipse projected on one plane which is normal and another plane which is parallel, respectively, to said test surface, said characteristic parameters being used in said procesing step for discriminating whether said one particular flaw is one of a volumetrictype defect, a planar defect and a combination of asid volumetric-type and planar defects.

4. The method as claimed in claim 1, wherein said position changing step comprises the step of appointing two additional positions of said transducer based on an angular direction of said major axis with respect to said reference system, said two additional positions of said transducer being used for detecting the path difference of said one particular flaw so as to determine the thickness of said one particular flaw.

* * * * *